(12) United States Patent
Wiemker et al.

(10) Patent No.: US 9,833,213 B2
(45) Date of Patent: Dec. 5, 2017

(54) ARIADNE WALL TAPING FOR BRONCHOSCOPIC PATH PLANNING AND GUIDANCE

(75) Inventors: Rafael Wiemker, Kisdorf (DE); Tobias Klinder, Uelzen (DE); Martin Bergtholdt, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 563 days.

(21) Appl. No.: 13/978,198

(22) PCT Filed: Jan. 12, 2012

(86) PCT No.: PCT/IB2012/050159
§ 371 (c)(1),
(2), (4) Date: Nov. 7, 2013

(87) PCT Pub. No.: WO2012/095809
PCT Pub. Date: Jul. 19, 2012

(65) Prior Publication Data
US 2014/0055584 A1    Feb. 27, 2014

Related U.S. Application Data

(60) Provisional application No. 61/432,706, filed on Jan. 14, 2011.

(51) Int. Cl.
*A62B 1/04*      (2006.01)
*A61B 6/00*      (2006.01)
(Continued)

(52) U.S. Cl.
CPC ........ *A61B 6/5294* (2013.01); *A61B 1/00045* (2013.01); *A61B 6/032* (2013.01);
(Continued)

(58) Field of Classification Search
IPC ........................................................ A61B 1/00
See application file for complete search history.

(56) References Cited

U.S. PATENT DOCUMENTS

| 5,440,393 A | * | 8/1995 | Wenz | ................. | G01B 11/2441 348/66 |
| 7,945,310 B2 | * | 5/2011 | Gattani | .............. | A61B 1/00039 600/117 |

(Continued)

FOREIGN PATENT DOCUMENTS

| CN | 1823349 A | 8/2006 |
| DE | 102007056800 | 6/2009 |

(Continued)

OTHER PUBLICATIONS

J.D. Gibbs et al., "3D MDCT-Based System for Planning Peripheral Bronchoscopic Procedures", Computers in Biology and Medicine, New York, NY, US, vol. 39, No. 3, Mar. 1, 2009, pp. 266-279.

*Primary Examiner* — Tracy Y Li

(57) ABSTRACT

A method, system and program product are provided for planning an intervention procedure in a body lumen. A CT scan of the body lumen is performed. A virtual rendering is created of the inside of the body lumen corresponding to an interventional camera image. Then a virtual tape corresponding to a planned path for the intervention procedure is projected onto a wall of the body lumen. The virtual tape is projected onto the lumen wall, which is relatively distant from the camera point on the virtual rendering, so the tape does not appear to oscillate like a central thread. Also, since the virtual tape is located on the lumen wall, it does not occlude the center of the lumen, allowing a user to better visualize the lumen during planning, during fly through, and even during an actual intervention.

20 Claims, 3 Drawing Sheets

(51) Int. Cl.
  *G06T 19/00* (2011.01)
  *A61B 1/00* (2006.01)
  *G06T 7/00* (2017.01)
  *G06T 17/00* (2006.01)
  *A61B 1/267* (2006.01)
  *A61B 6/03* (2006.01)
  *A61B 90/00* (2016.01)
  *A61B 34/10* (2016.01)

(52) U.S. Cl.
  CPC ............... *A61B 6/466* (2013.01); *A61B 6/52* (2013.01); *A61B 90/37* (2016.02); *G06T 7/0012* (2013.01); *G06T 17/00* (2013.01); *G06T 19/00* (2013.01); *A61B 1/2676* (2013.01); *A61B 6/03* (2013.01); *A61B 2034/107* (2016.02); *A61B 2090/365* (2016.02); *A61B 2090/366* (2016.02); *G06T 2210/41* (2013.01)

(56) References Cited

U.S. PATENT DOCUMENTS

| 8,028,338 | B1* | 9/2011 | Schneider ............ G06F 21/564 713/188 |
| 8,199,984 | B2 | 6/2012 | Mori et al. |
| 9,037,215 | B2 | 5/2015 | Higgins et al. |
| 2005/0182295 | A1* | 8/2005 | Soper .................. A61B 1/0008 600/117 |
| 2010/0041949 | A1* | 2/2010 | Tolkowsky .......... A61B 1/0052 600/109 |
| 2010/0272318 | A1* | 10/2010 | Cabiri ................ A61B 1/00096 382/106 |
| 2012/0063644 | A1 | 3/2012 | Popovic |

FOREIGN PATENT DOCUMENTS

| JP | H10234662 A | 9/1998 |
| JP | 2009056238 A | 3/2009 |
| WO | WO2005008591 | 1/2005 |
| WO | WO2009103046 | 8/2009 |

\* cited by examiner

ARIADNE WALL TAPING FOR BRONCHOSCOPIC PATH PLANNING AND GUIDANCE

The invention relates to the field of medical imaging and more particularly to a method, system and computer program product for projecting a tape onto a wall of a body lumen for path planning and guidance Bronchoscopies with or without transbronchial biopsies are a common interventional procedure, in which a bronchoscope camera is advanced into the tracheobronchial airway tree for diagnostic and optionally therapeutic purposes. In order to assist the planning, as well as the real-time guidance of such an intervention, a prior thoracic Computed Tomography (CT) scan of the patient may be used to compute virtual endoluminal renderings 10 which closely resemble the optical camera images from the real bronchoscope. The CT scan, as well as the virtual endoluminal renderings derived from it can be used to plan the path to a certain anomaly, tumor, lymph node, airway constriction, and the like.

As shown in FIG. 1, a planned path from the trachea to the pulmonary target may be overlayed over the virtual endoluminal rendering 10 as a thin line 20 in the center of the airway 15 called an Ariadne thread. This line 20, however can severely occlude the view into the center of the airway which the physician is to follow. Also, the central path line 20 has no visual depth cues for the user, and its three-dimensional course is therefore difficult to interpret. Moreover, since the central path line 20 typically runs very close to the camera point, the path can appear to strongly oscillate.

The present invention provides a method, system, and program product for planning an intervention procedure in a body lumen.

According to one embodiment, a method is provided for planning an intervention procedure in a body lumen. A CT scan of the body lumen is performed. A virtual rendering is created of the inside of the body lumen corresponding to an interventional camera image. Then a virtual tape corresponding to a planned path for the intervention procedure is projected onto a wall of the body lumen. The virtual tape is projected onto the lumen wall, which is relatively distant from the camera point on the virtual rendering, so the tape does not appear to oscillate like a central thread. Also, since the virtual tape is located on the lumen wall, it does not occlude the center of the lumen, allowing a user to better visualize the lumen during planning, during fly through, and even during an actual intervention.

According to one embodiment, the virtual tape is projected onto the lumen wall at each point along the planned path orthogonal to the local path with a constant included angle. Thus, as the body lumen decreases in size, the virtual tape 420 becomes narrower. This tape narrowing provides a visual depth cue for a user, better enabling the user to interpret the three-dimensional course of the body lumen 10.

According to one embodiment, the virtual tape is painted as a translucent overlay to allow appraisal of the underlying body lumen wall.

According to one embodiment the virtual tape is projected in a predetermined direction, such as ventral or dorsal to provide an indication of an orientation of the virtual rendering.

According to one embodiment, two virtual tapes are painted onto the body lumen wall, one in a ventral direction and the other in a dorsal direction, and the virtual tapes are color coded to indicate their respective directions.

According to one embodiment the body lumen is a tracheobronchial airway. In an alternative embodiment, the body lumen is a colon. In other embodiments, the body lumen may be another body structure that provides a channel in a tubular organ.

According to one embodiment a method is provided for guiding an intervention device during an intervention procedure in a body lumen. An image from a camera on an intervention instrument is displayed on a display. The planned intervention path is determined. Then, a virtual tape is projected onto a wall of the body lumen from the planned path on the camera image.

According to one embodiment, a system is provided for planning an intervention procedure in a body lumen. The system comprises: a processor; a memory operably connected with the processor; and a display operably connected with the processor; wherein the memory has encoded thereon a modeling program, which is executed by the processor to generate a virtual rendering of a body lumen from pre-procedural scans and project a virtual tape onto a lumen wall in the virtual rendering indicating a procedural path through the lumen.

According to one embodiment the system further comprises an intervention instrument having a camera, wherein the camera provides an image of a body lumen to the processor, and the processor displays the image on the display with a virtual tape projected onto a wall of the lumen indicating a planned intervention path. According to one embodiment, the instrument is a bronchoscope.

According to one embodiment, a computer program product is provided for planning an intervention procedure in a body lumen. The computer program product comprises a computer-readable program storage medium having encoded thereon: program code for performing a CT scan of the body lumen; program code for creating a virtual rendering of the inside of the body lumen corresponding to an interventional camera image; and program code for projecting onto a wall of the body lumen, a virtual tape corresponding to a planned path for the intervention procedure.

The features and advantages of the invention will be more clearly understood from the following detailed description of the preferred embodiments when read in connection with the accompanying drawing. Included in the drawing are the following figures.

The present invention provides a method, system, and program product for planning an intervention procedure in a body lumen.

Figure 1:
FIG. 1 is a virtual rendering of a traecheobronchial airway with a virtual central path thread according to the prior art.
Figure 2:
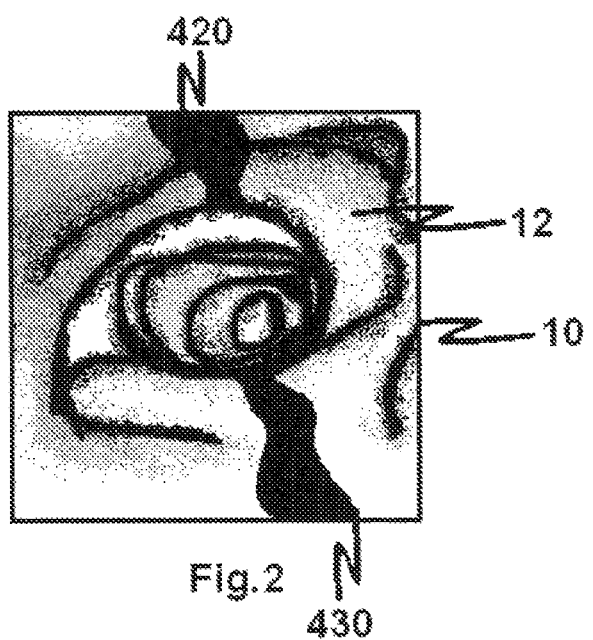
FIG. 2 is a virtual rendering of a traecheobronchial airway with tapes projected onto the ventral and dorsal walls of the airway according to various embodiments of the present invention.
Figure 4:
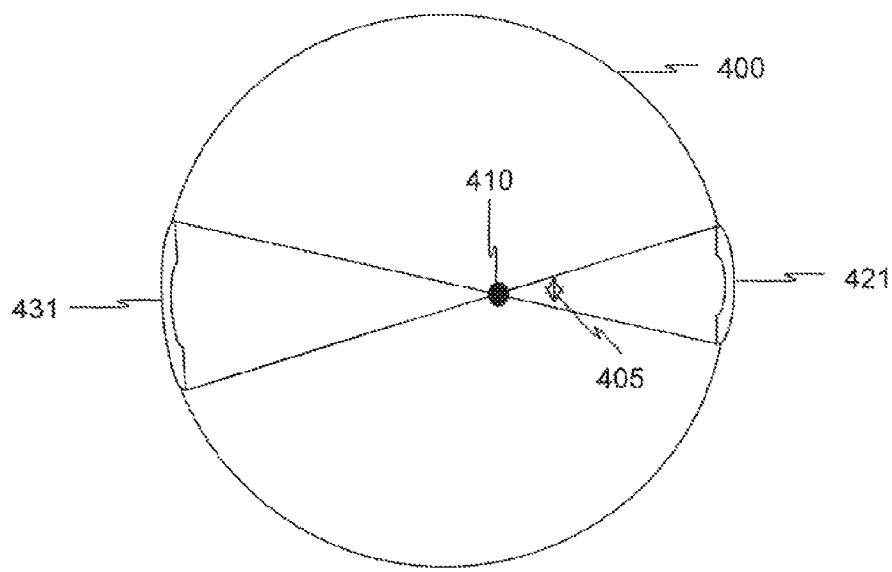
FIG. 4 is a diagram of a projection of tapes onto the walls of a virtual rendering orthogonal to a local path of an airway intervention.

According to one embodiment of the present invention, a virtual tape 420 is projected onto a lumen wall 12 of a virtual rendering of a body lumen 10, as shown in FIG. 2. A central path 410 of the body lumen 10, which is the path of the virtual thread 20 in existing methods, is located using known methods. The virtual tape 420 comprises a plurality of tape segments 421. As shown in FIG. 4, each tape segment 421 is created by projecting from a point on the central path 410 onto the lumen wall 12 orthogonal to the central path at an opening or included angle 405. Each segment comprises the space between the lines forming the included angle 405 at the z-axis position along the central path 410. The segments are combined to form a continuous tape 420 painted onto the lumen wall 12.

The virtual tape 420 is projected onto the lumen wall 12 which is relatively distant from the camera point on the virtual rendering, so the tape does not appear to oscillate like a central thread 20. Also, since the virtual tape 420 is located on the lumen wall 12, it does not occlude the center of the lumen, allowing a user to better visualize the lumen 10 during planning, during fly through, and even during an actual intervention.

According to one embodiment of the present invention, the included angle 405 is a constant angle for every point along the central path 410. Thus, as the body lumen decreases in size, the virtual tape 420 becomes narrower. This tape narrowing provides a visual depth cue for a user, better enabling the user to interpret the three-dimensional course of the body lumen 10.

According to one embodiment of the present invention, the virtual tape 420 is painted as a translucent overlay. This allows a user to visualize the underlying lumen wall 12 and any structures thereon.

According to one embodiment of the present invention, the virtual tape 420 is projected in a predetermined direction to provide an indication of an orientation of the virtual rendering. For example, the tape 420 may be projected from the center line 410 in a ventral direction. The tape may alternatively be projected in a dorsal direction or any other pre-determined direction.

According to one embodiment of the present invention, two virtual tapes 420, 430 are projected from the center line 410 of the body lumen 10. These two tapes 420, 430 may be color coded to provide an orientation reference. For example, a first tape 420 is projected in the ventral direction of the patient rendering and color coded green, while a second virtual tape 430 is projected in a dorsal direction of the patient rendering and color coded red.

While the foregoing description has been focused on a virtual rendering 10 constructed from a pre-procedural CT scan, it should be understood that a virtual tape may also be projected onto a lumen wall from an actual camera image during a procedure.

Figure 3:
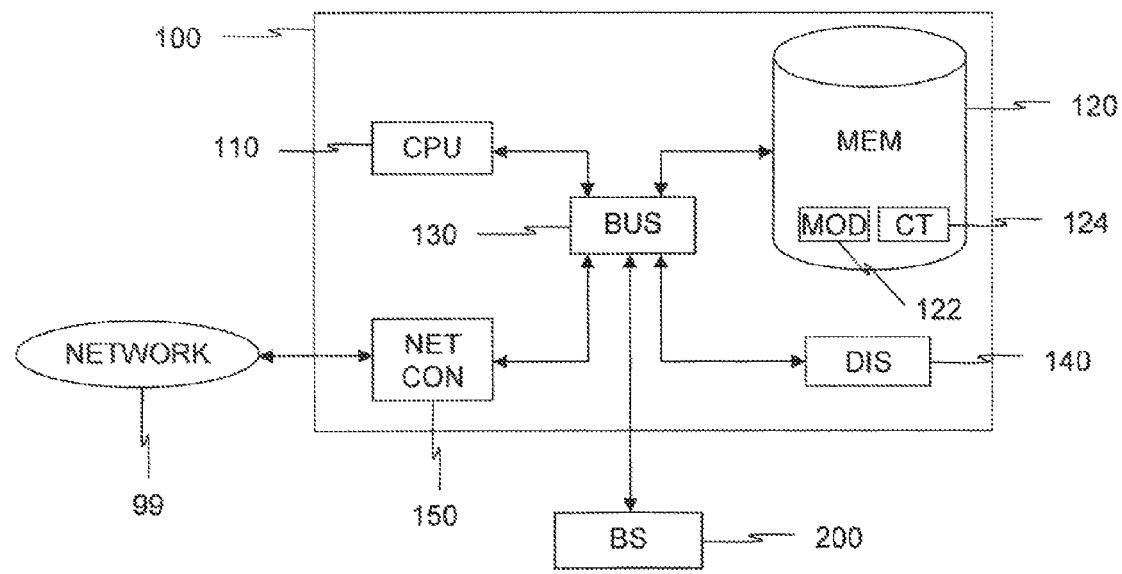
FIG. 3 is a block diagram of a system for planning an intervention procedure in a body lumen according to an embodiment of the present invention.

Referring now to FIG. 3, a system 100 is shown for planning an intervention procedure in a body lumen. According to one embodiment, the system 100 may realized in an imaging workstation, such as an Extended Brilliance Workspace (EBW) from Philips Electronics, N. V., Eindhoven, Netherlands. The EBW provides a graphical user interface which combines nuclear imaging such as Single Photon Emission Computer Tomography (SPECT) with Computer Tomography (CT).

According to one embodiment, the system 100 comprises a general purpose computer or a custom computing device. The system 100 comprises a central processing unit 110 that is operably connected with a memory 120 through a system bus 130 or the like. The processing unit 110 may be may be any device capable of executing program instructions, such as one or more microprocessors. The memory may be any volatile or non-volatile memory device, such as a removable disc, a hard drive, a CD, a Random Access Memory (RAM), a Read Only Memory (ROM), or the like, or any combination thereof.

A display 140 is also operably connected to the processor 110. The display may be any monitor, screen, or the like suitable for presenting a graphical user interface (GUI) capable of presenting medical images.

A modeling program 122 is encoded on the memory 120. The modeling program generates a three dimensional model of anatomical features from image data such as CT scans. The modeling program 122 may also create a rendering of the anatomical features from various perspectives, such as a rendering that closely resembles a view of a tracheobraonchial airway tree from within the airway like the view from a bronchoscope camera, for example. The modeling program can also render images of other body lumens from within the lumens.

The modeling program 122 can identify a central path 410 (FIG. 4) within a body lumen. Then, the modeling program can project a virtual tape onto an image of the lumen wall 12 from the central path, perpendicular to the central path. The virtual tape may be used for planning a path to an anomaly, airway restriction, tumor, or the like.

According to one embodiment of the present invention, pre-procedural CT scans 124 are encoded on memory 120 to be used for creating the three-dimensional anatomical model. The CT scans 124 may be uploaded from a storage device, such as a CD-ROM, or the like. Alternatively, the CT scans 124 may be received through a network, such as the internet or an intranet, or the like. To accomplish this, a network connection may be operably connected to the memory 120 through a system bus 130 or the like.

Figure 5:
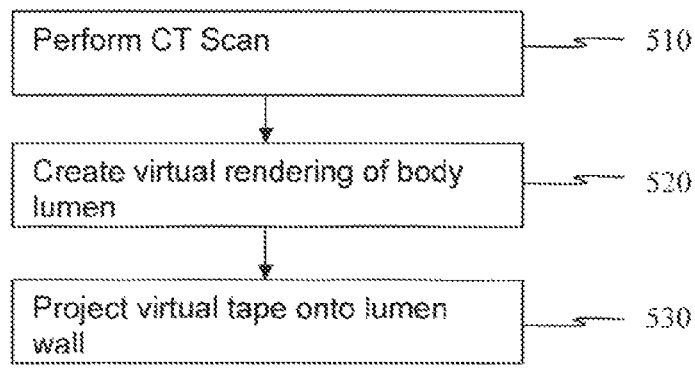
FIG. 5 is a flow diagram of a method for planning an intervention procedure in a body lumen according to an embodiment of the present invention.

Referring now to FIG. 5, a method is shown for planning an intervention procedure in a body lumen. A pre-procedure CT scan is performed (Step 510). The scan 124 is then loaded into an imaging system, such as the Philips EBW. The CT scanner may be integral with the imaging system, and provide the scan directly. Alternatively, the scan may be sent to the imaging system through a network, or the scan may be recorded on a recording media, such as a CD-ROM, flash drive, or the like, which can be inserted in an appropriate drive or connector on the imaging system for access by the processor 110.

From the CT scan 124, the imaging system 100 creates a virtual rendering of a body lumen 10 such as a tracheobronchial airway tree, using a modeling program 122 (Step 520). As previously described, the virtual rendering may be created by the processor 110 executing a modeling program 122 encoded on memory 120. The virtual rendering is displayed on the display 140.

The system 100 then projects a virtual tape 420 onto a wall 12 of the lumen 10 (Step 530) indicating a planned path for an intervention procedure. The user typically identifies a target in the CT image, e.g., a lesion, and the modeling program calculates a path from trachea to the lesion following the airway. Alternatively, the modeling program 122 may find the target automatically. According to another embodiment, a user may also manually click in the image to define some points and then the modeling program 122 calculates an optimal path through those points. The calculated path can also manipulated by editing the curve.

Figure 6:
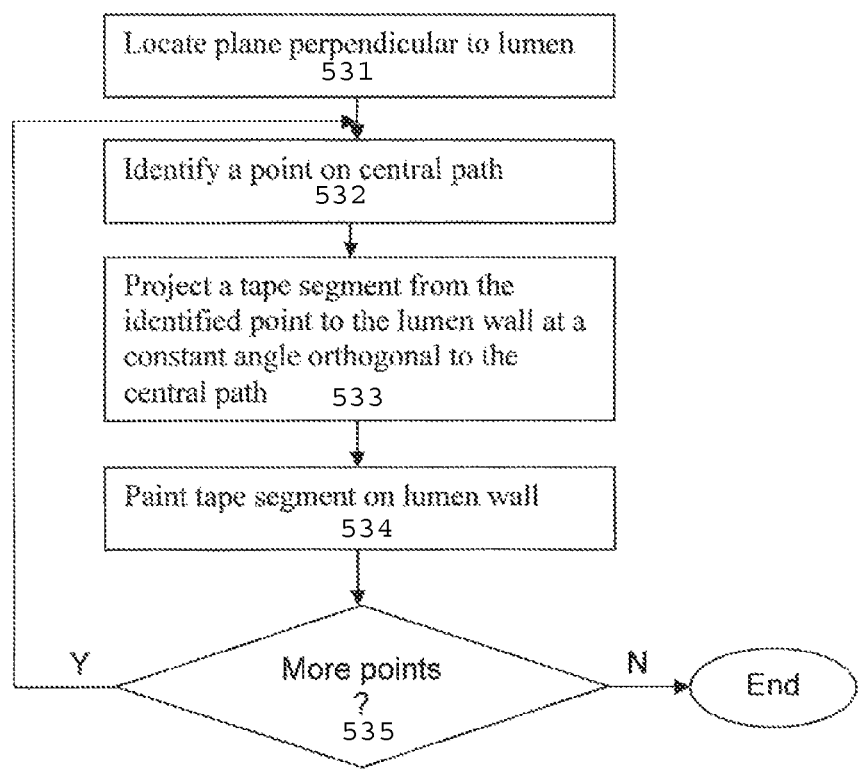
FIG. 6 is a flow diagram of a method for projecting a virtual tape onto a lumen wall of an image for an intervention procedure according to an embodiment of the present invention.

FIG. 6 is a flow diagram of a method for projecting a virtual tape onto a lumen wall according to one embodiment of the present invention. First, the processor 110 executing the modeling program 122 locates a plane perpendicular to the lumen 10 (Step 531). That is, a plane is identified in a three-dimensional image space which is perpendicular to the lumen.

The system 100 identifies a point that is on the central path 410 (Step 532). This may be accomplished, for example, by constructing a best fit circle for the section of the lumen in the identified plane and calculating the center of that circle. Alternatively, this may be accomplished by calculating a distance map based on the segmented tree. The distance map is a gray scale image as the CT but each voxel contains in this case the closest distance information from the boundary of the segmented airway tree. Within one cross section the point with the largest distance to the boundary is the centerpoint. Then, one can trace along the path by growing in the direction of the voxel that has the highest distance value.

The system 100 projects a tape segment 421 form the point on the central path 410 onto the lumen wall 12 at a constant included angle 405 orthogonal to the central path 410 (step 533). That is, in the plane perpendicular to the lumen 10, the system 100 constructs an angle 405 from the central point on the central path 410 to the lumen wall 12, and constructs a tape segment on the wall at the intersections of the angle 405 and the lumen wall 12. In one embodiment the angle 405 is about 5°. As described above, the projection may be in a specific direction, such as ventral.

The system 100 paints the tape segment on the lumen wall 12 (step 534). That is, the segment of the lumen wall 12 within the included angle 405 is painted a specified color, such as green or red, for example. It will be understood by those skilled in the art, that, although the segment is described as lying in a plane perpendicular to the central path, the segment actually has a minimal thickness consistent with a pixel width of the imaging system. Thus a segment of lumen wall 12 having a thickness of a pixel is painted a specified color to contrast with the lumen wall 12. According to one embodiment, the tape segment is painted as a translucent overlay to allow for viewing the underlying lumen wall 12.

After the segment is painted, the system determines whether or not additional points are present on the central path 410 (Step 535). If there are additional points, then the system identifies the new point (step 532) and repeats steps 533-535 for the new point. If there are not additional points, then the process ends.

The invention can take the form of an entirely hardware embodiment, an entirely software embodiment or an embodiment containing both hardware and software elements. In an exemplary embodiment, the invention is implemented in software, which includes but is not limited to firmware, resident software, microcode, etc.

Furthermore, the invention may take the form of a computer program product accessible from a computer-usable or computer-readable medium providing program code for use by or in connection with a computer or any instruction execution system or device. For the purposes of this description, a computer-usable or computer readable medium may be any non-transient apparatus that can contain or store the program for use by or in connection with the instruction execution system, apparatus, or device.

The foregoing method may be realized by a program product comprising a machine-readable medium having a machine-executable program of instructions, which when executed by a machine, such as a computer, performs the steps of the method. This program product may be stored on any of a variety of known machine-readable medium, including but not limited to compact discs, floppy discs, USB memory devices, and the like.

The medium can be an electronic, magnetic, optical, electromagnetic, infrared, or semiconductor system (or apparatus or device). Examples of a computer-readable medium include a semiconductor or solid state memory, magnetic tape, a removable computer diskette, a random access memory (RAM), a read-only memory (ROM), a rigid magnetic disk an optical disk. Current examples of optical disks include compact disk-read only memory (CD-ROM), compact disk-read/write (CD-R/W) and DVD.

The preceding description and accompanying drawing are intended to be illustrative and not limiting of the invention. The scope of the invention is intended to encompass equivalent variations and configurations to the full extent of the following claims.

What is claimed is:

1. A method for planning an intervention procedure in a body lumen, comprising:
    performing a CT scan of the body lumen;
    creating a virtual rendering of the inside of the body lumen corresponding to an interventional camera image; and
    projecting onto a wall of the body lumen in the virtual rendering, a virtual tape corresponding to a planned path for the intervention procedure.

2. The method of claim 1, wherein the virtual tape is projected from a centerline of the planned path onto the lumen wall at each point along the planned path orthogonal to the local path with a constant included angle.

3. The method of claim 1, wherein the virtual tape is painted as a translucent overlay to allow appraisal of the underlying body lumen wall.

4. The method of claim 1, wherein the virtual tape is projected in a predetermined direction to provide an indication of an orientation of the virtual rendering.

5. The method of claim 1 wherein two virtual tapes are painted onto the body lumen wall, one in a ventral direction and the other in a dorsal direction, and the virtual tapes are color coded to indicate their respective directions.

6. The method of claim 1, wherein the body lumen is a tracheobronchial airway.

7. The method of claim 1, wherein the body lumen is a colon.

8. A method of guiding an intervention device during an intervention procedure in a body lumen, comprising:
    displaying an image from a camera on an intervention instrument on a display;
    determining a planned intervention path; and
    projecting a virtual tape onto a wall of the body lumen from the planned path on the camera image.

9. The method of claim 8, wherein the virtual tape is projected from a centerline of the planned path onto the lumen wall at each point along the planned path orthogonal to the local path with a constant included angle.

10. The method of claim 8, wherein the virtual tape is painted as a translucent overlay to allow appraisal of the underlying body lumen wall.

11. The method of claim 8, wherein the virtual tape is projected in a predetermined direction to provide an indication of an orientation of the virtual rendering.

12. The method of claim 8 wherein two virtual tapes are painted onto the body lumen wall, one in a ventral direction and the other in a dorsal direction, and the virtual tapes are color coded to indicate their respective directions.

13. A system for planning an intervention procedure in a body lumen, comprising:

a processor;

a memory operably connected with the processor; and a display operably connected with the processor;

wherein the memory has encoded thereon a modeling program, which is executed by the processor to generate a virtual rendering of a body lumen from pre-procedural scans and project a virtual tape onto a lumen wall in the virtual rendering indicating a planned procedural path through the lumen.

14. The system of claim 13, wherein the virtual tape is projected from a centerline of the planned procedural path onto the lumen wall at each point along the planned path orthogonal to the local path with a constant included angle.

15. The system of claim 13, wherein the virtual tape is painted as a translucent overlay to allow appraisal of the underlying body lumen wall.

16. The system of claim 13, wherein the virtual tape is projected in a predetermined direction to provide an indication of an orientation of the virtual rendering.

17. The system of claim 13, wherein two virtual tapes are painted onto the body lumen wall, one in a ventral direction and the other in a dorsal direction, and the virtual tapes are color coded to indicate their respective directions.

18. The system of claim 13, further comprising an intervention instrument having a camera, wherein the camera provides an image of a body lumen to the processor, and the processor displays the image on the display with a virtual tape projected onto a wall of the lumen indicating a planned intervention path.

19. The system of claim 18, wherein the intervention instrument is a bronchoscope.

20. A computer program product comprising a non-transient computer-readable program storage medium having encoded thereon:

program code for performing a CT scan of the body lumen;

program code for creating a virtual rendering of the inside of the body lumen corresponding to an interventional camera image; and program code for projecting onto a wall of the body lumen, a virtual tape corresponding to a planned path for the intervention procedure.

* * * * *